(12) United States Patent
Schentag et al.

(10) Patent No.: US 12,343,374 B2
(45) Date of Patent: Jul. 1, 2025

(54) ENHANCEMENT OF ANTIBACTERIAL ACTIONS OF A DEPSIPEPTIDE ANTIBIOTIC USING SYNERGISTIC AMOUNTS OF BORIC ACID

(71) Applicant: KYOTO BIOPHARMACEUTICALS, INC, Kyoto (JP)

(72) Inventors: Jerome J. Schentag, Buffalo, NY (US); Hirofumi Nakajima, Kobe (JP)

(73) Assignee: KYOTO BIOPHARMACEUTICALS, INC., Kyoto (JP)

( * ) Notice: Subject to any disclaimer, the term of this patent is extended or adjusted under 35 U.S.C. 154(b) by 860 days.

(21) Appl. No.: 17/251,367

(22) PCT Filed: Jun. 12, 2019

(86) PCT No.: PCT/IB2019/054921
§ 371 (c)(1),
(2) Date: Dec. 11, 2020

(87) PCT Pub. No.: WO2019/239352
PCT Pub. Date: Dec. 19, 2019

(65) Prior Publication Data
US 2021/0244790 A1    Aug. 12, 2021

Related U.S. Application Data

(60) Provisional application No. 62/684,316, filed on Jun. 13, 2018.

(51) Int. Cl.
| | | |
|---|---|---|
| A61K 38/15 | (2006.01) |
| A61K 9/00 | (2006.01) |
| A61K 9/06 | (2006.01) |
| A61K 33/22 | (2006.01) |
| A61K 47/10 | (2017.01) |
| A61K 47/14 | (2017.01) |
| A61K 47/18 | (2017.01) |
| A61K 47/38 | (2006.01) |
| A61P 31/04 | (2006.01) |

(52) U.S. Cl.
CPC ............ *A61K 38/15* (2013.01); *A61K 9/0014* (2013.01); *A61K 9/0048* (2013.01); *A61K 9/06* (2013.01); *A61K 33/22* (2013.01); *A61K 47/10* (2013.01); *A61K 47/14* (2013.01); *A61K 47/183* (2013.01); *A61K 47/38* (2013.01); *A61P 31/04* (2018.01)

(58) Field of Classification Search
None
See application file for complete search history.

(56) References Cited

FOREIGN PATENT DOCUMENTS

| | | |
|---|---|---|
| EP | 2047857 A1 | 4/2009 |
| WO | 2013042140 A2 | 3/2013 |
| WO | 2016205574 A1 | 12/2016 |

OTHER PUBLICATIONS

Guest, R.T. (2009) Albumin in R.C. Rowe, P. J. Sheshkey, and M. E. Quinn (Eds) Handbook of Pharmaceutical Excipients, 6th ed., pp. 14-16, Pharmaceutical Press (Year: 2009).*
Itoh H, et al. Total Synthesis and Biological Mode of Action of WAP-8294A2: A Menaquinone-Targeting Antibiotic. Journal of Organic Chemistry, 2017;83(13):6924-6935.
Schubert, David M. et al, "Antimicrobial Properties of Boron Derivatives"; ACS Symposium Series 967; Chapter 20; p. 412-435; American Chemical Society 2007; Washington, D.C.
Chihiro Katsukawa et a l.; "A Study of the Antibacterial Effect of Boric Acid"; Chemotherapy: vol. 41—No. 11. pgs. 1160-66;, Nov. 1993; Osaka Prefectural Bandai Clinic for STD.
Demet Celebi et al; "Effects of Boric Acid and Potassium Metaborate on Cytokine Levels and Redox Stress Parameters in a Wound Model Infected with Methicillin-resistant *Staphylococcus aureus*"; Molecular Medicine Report; vol. 26 3 2022; pp. 1-11; Spandidos Publications; Jun. 2022.
Hager Muftah et al; "A Comparative Evaluation of *Juniperus* Species of Antimicrobial Magistrals"; Pak. J. Pharm. Sci.; vol. 33, No. Jul. 4, 2020, pp. 1443-1449.
Yilmaz, Murat Tolga; "Minimum Inhibitory and Minimum Bactericidal Concentrations of Boron Compounds Against Several Bacterial Stains". Turkish Journal of Medical Sciences' vol. 42, No. 8, Article 10.

* cited by examiner

*Primary Examiner* — Christina Bradley
(74) *Attorney, Agent, or Firm* — Henry D. Coleman; R. Neil Sudol

(57) ABSTRACT

An external or topical formulation for treatment or prevention of infections involving body surfaces using a depsipeptide antibiotic drug such as lotilibcin having improved efficacy and safety is provided. The antibacterial effect of lotilibcin tested in infectious models is substantially enhanced by addition of boric acid in a low concentration of an additive level which does not produce any pharmacological activity by itself, thereby offering a formulation for external preparations having improved safety due to a decrease in dose, dosing period, and dosing frequency.

15 Claims, 3 Drawing Sheets

ENHANCEMENT OF ANTIBACTERIAL ACTIONS OF A DEPSIPEPTIDE ANTIBIOTIC USING SYNERGISTIC AMOUNTS OF BORIC ACID

RELATED APPLICATIONS

This application is a United States national phase patent application based upon international patent application number PCT/IB2019/054921 filed Mar. 14, 2014, which claims the benefit of priority of U.S. provisional application No. 62/684,316, filed Jun. 13, 2018, the entire contents of which two applications are incorporated by reference in their entirety herein.

FIELD OF THE INVENTION

The present invention relates to depsipeptide antibiotic drug-containing (preferably lotilibcin or a pharmaceutically acceptable salt or stereoisomer thereof) external formulations for use in prevention or treatment of bacterial infections. Methods of using these formulations in the treatment of external infections in a patient or subject represent additional aspects of the present invention.

BACKGROUND ART

The history of antibacterial drugs which are effective for the treatment of bacterial infections covers nearly 80 years starting from 1941 when penicillin exhibited its clinical efficacy for the first time. From 1940's to 1960's, at least 15 types of antibacterial drugs (antibiotic drugs) were found from natural sources. After the beginning of 1960's, the development of new drugs has been predominantly carried out by synthetic methods based on a preexisting compound, resulting in an extreme decrease in the number of new antibiotics developed from natural sources. Thus, during the ages from 1980's to 2000's, only two examples of such drugs were successfully developed.

On the other hand, from a clinical aspect, as the frequency and number of antibacterial drugs have proliferated, drug-resistant bacteria to which antibiotics are tolerant appeared and spread across the world. This is particularly true in developed countries where antibiotic therapy and medical technology are advanced, the result being that the proportion of drug-resistant bacteria has dramatically increased since the 1980's.

Furthermore, as a result of biological development, drug-resistant bacteria have evolved to acquire multi-drug resistance in many countries, a significant clinical problem in and of itself which has complicated the development of new antibacterial drugs.

The bacterial infections which were considered problematic in the past were almost always hospital-acquired infections of in patients, but subsequent to 2000, a number of onset cases due to community-acquired infections in hospitals and health care facilities have been reported, producing an entirely new threat. One of the principal causes of the increased incidence of these infections is the nature of bacteria and the fact that that they can easily be transferred by their hosts to uninfected patients by contact with the skin of a new (naïve) host. Therefore, as one of the effective solutions to eliminating or at least reducing this problem, it is useful to provide an antibacterial preparation for external/topical use which exhibit excellent efficacy against external/topical bacterial infections, which presently have an extremely limited number of choices due to reliance on old-line bacterial drugs, and to oral preparations and injection preparations which have frequently been used for antibacterial treatments in the past.

Lotilibcin, which is a depsipeptide antibiotic having 12 amino acid residues, was found as an antibacterial drug effective against infections with Gram-positive cocci, particularly with methicillin-resistant *Staphylococcus aureus* (MRSA). Lotilibcin was isolated from a series of antibacterially active ingredients produced by *Lysobacter* sp. WAP-8294 strain as disclosed in U.S. Pat. No. 5,648,455, as well as Harad, et al., *J. Chromatogr. A*, 2001, Vol. 932, No. 1-2, pp. 75-81.

Unlike most conventional antibiotics which have been discovered and/or prepared from a natural source, lotilibcin has a unique nature biological profile that exhibits a strong antibacterial activity only on a very limited number of species of bacteria and usually only action against Gram-positive bacteria. In particular, lotilibcin reveals a bactericidal antibacterial activity on drug-resistant staphylococci such as MRSA and MRSE (methicillin-resistant *Staphylococcus epidermidis*) within two hours. Thus, lotilibcin is an anti-MRSA antibiotic having a short range antibacterial spectrum and a potent antibiotic property.

For practical use of lotilibcin in drug preparations, U.S. Pat. No. 5,648,455 discloses in Example 13 typical formulations for injections, oral preparations (tablets) and external preparations (ointments and eye drops) using conventional techniques.

For use of lotilibcin by injection or drip infusion, U.S. Pat. No. 7,968,588 shows a formula containing hydroxypropyl-β-cyclodextrin which can provide a dramatic improvement in safety and which is effective in treatment of systemic infections with a drug-resistant bacterium, particularly with MRSA. However, there is no disclosure therein with respect to a method of application to topical bacterial infections or topical formulations which exhibit enhanced and unexpected activity.

The present inventors investigated the possibility of using lotilibcin as a therapeutic drug for topical bacterial infections. As a practical matter, it was found difficult to put lotilibcin into a topical preparation for treatment of topical bacterial infections using the teaching from U.S. Pat. No. 5,648,455 which patent merely discloses general formulas, or U.S. Pat. No. 7,968,588 which teachings relate to parenteral formulations for drip infusion or injection, or other prior art for the following reasons.

As stated in U.S. Pat. No. 5,648,455 as one feature, lotilibcin is known to have a significantly enhanced antibacterial activity in a physiological environment in which a serum component exists. This is novel and unexpected. Almost all antibiotics are less active against bacteria when the interaction occurs in the presence of serum albumin. Therefore, lotilibcin exhibits an efficacy surpassing prior art antibacterial drugs in an animal infection model. However, when lotilibcin was administered with a dose which is the same as for existing antibacterial drugs or more using a formula known in the prior art as is disclosed in U.S. Pat. No. 5,648,455, it was found that although a pharmacological efficacy for lotilibcin equivalent to that of the prior art antibacterial drugs could be expected, maintaining the required drug concentration results in the appearance of toxicity, particularly in the form of irritating reactions or toxic reactions accompanied by histological alterations, resulting in the conclusion drawn that both of safety and efficacy cannot be secured simultaneously.

In addition, an incredibly large number of antibacterial drugs has been used/overused worldwide in the past for lengthy periods in a wide range of fields including medical care, stockbreeding, agriculture, forestry, and fisheries, microbiological evolution of bacteria which have been exposed to these drugs has accelerated in recent years, leading to bacterial mutation into drug-resistant bacteria acquiring a high degree of multi-drug resistance. Thus, with respect to lotilibcin which is a compound discovered more than twenty years ago, it was unexpected to scientifically demonstrate its efficacy as a therapeutic agent for topical bacterial infections intended for external use to a degree which significantly surpasses the efficacy of existing antibacterial drugs against present-day highly drug resistant bacteria.

Accordingly, the present inventor continued to investigate the use of lotilibcin in order to find a novel medical formulation for the purpose of applying lotilibcin externally for topical use in an effective and safe manner.

SUMMARY OF THE INVENTION

Problems to be Solved by the Present Invention

The problem to be solved by the present invention is to provide a formulation for a topical use or external composition which has high effectiveness and safety profile which comprises a naturally occurring depsipeptide antibiotic drug (preferably lotilibcin) having a targeted antibacterial spectrum range and potent antibiotic activity. Said formulation contains additive substances that synergistically enhance the anti-bacterial action of lotilibcin.

Means for Solving the Problem

Upon earnest investigations for solving the above-mentioned problem, the present inventors have discovered that the addition of boric acid in a low concentration which corresponds to an additive level having no antiseptic or antibiotic effect on its own makes it possible to prepare a depsipeptide antibiotic drug-containing formulation for external use having a high degree of effectiveness and safety, and accomplished the present invention.

Summary of Effects of the Invention

According to the present invention, by incorporating a low concentration of boric acid with depsipeptide antibiotics and, in particular, lotilibcin in various topical formations for external use to treat patients and subjects, it is possible to achieve a synergy in antibacterial activity which is superior to existing antibacterial drugs in topical bacterial infections. Said new compositions feature a significantly decreased effective concentration of a depsipeptide antibiotic drug, particularly lotilibcin, thereby providing an external preparation having a high degree of effectiveness and safety.

DETAILED DESCRIPTION OF THE INVENTION

Definition and Use of Terms

Figure 1:
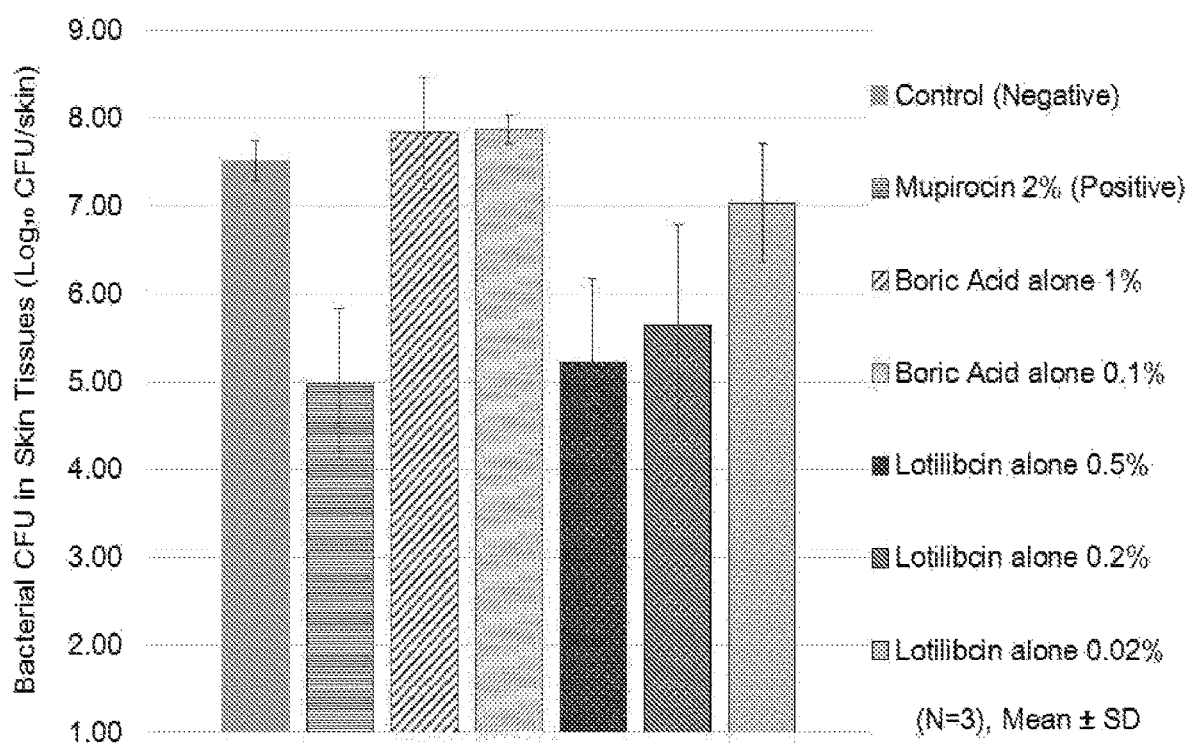
FIG. 1 A chart showing the result of an efficacy evaluation test (a preliminary test) by single dose application using experimental murine models infected with methicillin-resistant *Staphylococcus aureus* (MRSA) on the skin. The ordinate shows the result of efficacy obtained by applying a single dose of a test substance to the skin which has been inoculated by $1\times10^6$ CFU (colony forming units) of bacterial cells, excising the infected skin tissue after 24 hours, counting the number of CFUs in the skin tissue, and evaluating the efficacy by a decrease or increase in the number of CFUs. The abscissa shows the individual test substances.

The present invention will be explained below in detail. In the following description, percent (%) is percent by weight unless otherwise indicated within the context of its use. Concentrations (e.g., mg/mL or mM/ml, etc.) are also used to describe the present invention.

The following terms shall be used throughout the specification to describe the present invention. Where a term is not specifically defined herein, that term shall be understood to be used in a manner consistent with its use by those of ordinary skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges that may independently be included in the smaller ranges are also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Furthermore, the following terms shall have the definitions set out below.

The term "patient" or "subject" is used throughout the specification within context to describe an animal, generally a mammal, especially including a domesticated animal and preferably a human, to whom treatment, including prophylactic treatment (prophylaxis), with the compositions according to the present invention is provided. For treatment of those infections, conditions or disease states which are specific for a specific animal such as a human patient, the term patient refers to that specific animal. In most instances, the patient or subject of the present invention is a human patient of either or both genders.

The term "effective" is used herein, unless otherwise indicated, to describe an amount of a compound or component which, when used within the context of its use, produces or effects an intended result, whether that result relates to the prophylaxis and/or therapy of an infection and/or disease state, especially a bacterial infection including a MRSA or other infection as described herein within the context of its use or as otherwise described herein, including its use to produce a synergistic result or effect in certain instances. Under conditions of ordinary use in treatment of infectious disease, an antibiotic is considered to be effective if the bacterial organism treated with said antibiotic is killed or eliminated from the site of infection. An effective antibiotic used for sufficient time also results in improved health of tissues or the whole body. The term effective subsumes all other effective amount or effective concentration terms (including the term "therapeutically effective") which are otherwise described or used in the present application. The term "therapeutically effective concentration" is defined as the concentration or amount of the antibiotic agent sufficient to result in or produce preventative, healing, curative, stabilizing, ameliorative effect in the treatment of the treatment site or condition and may include reduction or elimination of MRSA.

Thus, provided herein are methods of killing a bacterium by contacting said bacteria with the antimicrobial composition provided herein. In one example, the bacterium killed is *Staphylococcus*. In some examples, the bacterium is killed within 10 minutes, within 15 minutes, within 20 minutes, or within 30 minutes (such as within 10-30 minutes, 10-20 minutes or 10-15 minutes) of contacting it with the antimicrobial composition. In some examples, not all of the bacteria contacted with the composition are killed, but the composition is still an antimicrobial composition. For example, in some examples at least 90%, at least 95%, at least 99%, at least 99.9%, at least 99.99%, or at least 99.999% of the microorganisms (such as an at least 10-fold, at least 20-fold, at least 30-fold, at least 40-fold, at least 50-fold, or at least 100-fold reduction) are killed within 10 minutes, within 20 minutes, or within 30 minutes (such as within 10-30 minutes, 10-20 minutes or 10-15 minutes) of contacting it with the antimicrobial composition.

The term "compound" is used herein to describe any specific compound or bioactive agent disclosed herein, including any and all stereoisomers (including diastereomers, individual optical isomers/enantiomers or racemic mixtures and geometric isomers), pharmaceutically acceptable salts and prodrug forms. The term compound herein refers to stable compounds. Within its use in context, the term compound may refer to a single compound or a mixture of compounds as otherwise described herein.

The term "pharmaceutically acceptable" as used herein means that the compound or composition is suitable for administration to a subject to achieve the treatments described herein, without unduly deleterious side effects considering the severity of the disease and necessity of the treatment.

The term "independently" is used herein to indicate that the variable, which is independently applied, varies independently from application to application.

The terms "about" and "approximately" are used as equivalents. Any numerals used in this application with or without about/approximately are meant to cover any normal fluctuations appreciated by one of ordinary skill in the relevant art. For example, as used herein, the term "approximately" or "about," as applied to one or more values of interest, refers to a value that is similar to a stated reference value. In certain embodiments, depending on context, the term "approximately" or "about" refers to a range of values that falls within 15%, 14%, 13%, 12%, 11%, 10%, 9%, 8%, 7%, 6%, 5%, 4%, 3%, 2%, 1%, or less in either direction (greater than or less than), more often 5% or less of the stated reference value unless otherwise stated or otherwise evident from the context (except where such number would exceed 100% of a possible value).

Topical Formulation, Topical Application

The term "topical formulation" is used to describe compositions according to the present invention which are administered externally to a patient or subject in topical dosage form. General formulations for topical delivery are described in Remington's Pharmaceutical Sciences, 18th Edition, Mack Publishing, p. 1288-1300 [1990]. Accordingly, in some embodiments, the extracts are formulated as a water-based gel or paste, ointment, cream (anhydrous or hydrous), lotion (anhydrous or hydrous), emulsion, spray, solution, aerosol, stick (solid cream), liquid band aid, powder, inhalation spray, nasal spray, basal drops, cheek drops, sublingual drops, eye drops or sprays, ear drops or sprays, and transdermal patches.

The term "topical application" is used to describe the administration of the compositions to an external surface of a patient or subject in the treatment of a disease state and/or condition otherwise described herein. It is contemplated that the compositions for topical application described above find use for both cosmetic and therapeutic purposes. Therapeutic uses are for treatment of infections often bacterial infections and in particular, drug resistant bacterial infections. In some embodiments, it is contemplated that the compositions described above are applied directly to the skin or other epithelial or epidermal surfaces of the body. The compositions may be applied one, two, three or more times each day as is appropriate for the indication. The amount applied is not generally important, but often a composition comprising from about 0.001 mg to 5.0 grams or more (often from at least about 1 mg to about 2 grams) may be applied to a given surface of the body per day in divided doses. As described above, the composition for topical use may comprise other components such as antiseptics, surface active agents, adjuvants, carriers, other active ingredients, etc. and be in the form of a gel, cream, ointment lotion or liquid, among others.

The term "antibacterial" is used herein to define a compound that destroys bacteria or inhibits the growth of bacteria and may be referred to as an antibiotic or bacteriostat.

The term "antiseptic" is defined as an antimicrobial substance that may be applied topically to the surface of the patient. In the present embodiment, Boric acid is most commonly classified as an antiseptic substance. According to the teachings of the present invention, the use of the antiseptic boric acid in combination with antibiotics such as depsipeptides, especially lotilibcin may provide synergistic improvements in activity and more efficacy against certain bacteria such as *staphylococcus*.

Definition of Acne

As used herein the term "acne" refers to a condition selected from the group consisting of acne vulgaris, acne venenata, cystic acne, acne fulminans, acne papulosa, acne pustulosa, acne caused by MRSA, and nodulocystic acne. The topical formulation of claim 1 used in the treatment of acne, may involve additional formulation components that are already used as anti-acne treatments. When used in this composition, anti-acne agents useful in combination are selected from the group consisting of benzoyl peroxide, salicylic acid and a retinoid in combination with said depsipeptide antibiotic and said antiseptic boric acid.

Definition of Wound and Wound Infection

As used herein, the term "wound" is defined as an injury to any tissue, and the term "infected wound" or "wound infection" is defined as infection that usually occurs as a consequence of tissue injury, where said injury includes burns, lacerations, abrasions, bites, surgical wounds, puncture wounds, ulcers, including but not limited to acute and chronic wounds from complicated skin and soft tissue infection (cSSTI), acute and chronic wounds from skin and skin structure infection (SSSI) venous stasis ulcers, diabetic ulcers, pressure ulcers, post-surgical ulcers, post traumatic ulcers and spontaneous ulcers.

Definition of Synergy and Consequential Benefits Thereof

As used herein, the terms "synergy" and "synergistic activity" refer to the interaction of two substances when they are combined or used together for a specific purpose in medicine. When substances are combined, the action of one substance in the presence of the other substance can be either the same as if one were doubled and thus the action is double, which is defined as additive. In additive interactions, there is no benefit to the second substance beyond reproducing what twice as much of the other would produce. Synergy occurs when the resulting action from combination of two substances is more than the aforementioned doubling. Ordinary definitions of synergy encompass more than two-fold action of combination, and in practical use usually mean more than fourfold to more than tenfold enhancement of the components when combined.

In addition to beneficial actions such as killing of bacteria at the site of the infection, beneficial actions of synergy between antibiotics and antiseptics and endogenous molecules in a wound infection include stimulating fibroblast migration, stimulating elastin production, reducing expression of inflammatory factors and up-regulating specific genes, reducing fine lines in the skin, normalizing skin color, balancing skin pigmentation, reducing skin redness, increasing skin brightness, increasing skin water content and hydration, decreasing or normalizing the amount of sebum in the skin, decreasing production of melanin, increasing collagen protein production, increasing collagen gene expression, increasing adult stem cell proliferation, increasing cellular metabolism of carbohydrates, increasing cellular metabolism of lipids, prevention of apoptosis, increasing angiogenesis, upregulation the cell cycle of cells, increasing angiogenesis, increasing follicular development.

Synergistic Combination of Depsipeptide Lotilibcin and Boric Acid for External Use The present invention relates to a depsipeptide antibiotic drug-containing formulation for use by topical application in prevention or treatment of bacterial infections, more often bacterial wound infections, which further contains at least 0.01% by weight of boric acid. In particular preferred embodiments, the concentration of boric acid ranges from at least about 5.0 mM/ml (about 313 μg/ml) to no more than about 40 mM/ml (about 2500 g/ml and the concentration of depsipeptide ranges from at least about 18 nM/ml (0.03 μg/ml) or at least about 152 nM/ml (0.25 μg/ml) to about 4881 nM/ml (about 8.0 μg/ml).

The depsipeptide antibiotic drug which is in interest in the present invention is a compound having a peptide structure generally formed by combining amino acid residues through an amide bond (—CONHR—, R is the sidechain of an amino acid) in which at least one amide bond is replaced by an ester bond (—COOR—). Preferably, the depsipeptide antibiotic drug which is used in the present invention has a molecular structure constituted by 12 amino acid residues, and more preferably, it is lotilibcin having the following structural formula (1) or a pharmaceutically acceptable salt or stereoisomer thereof.

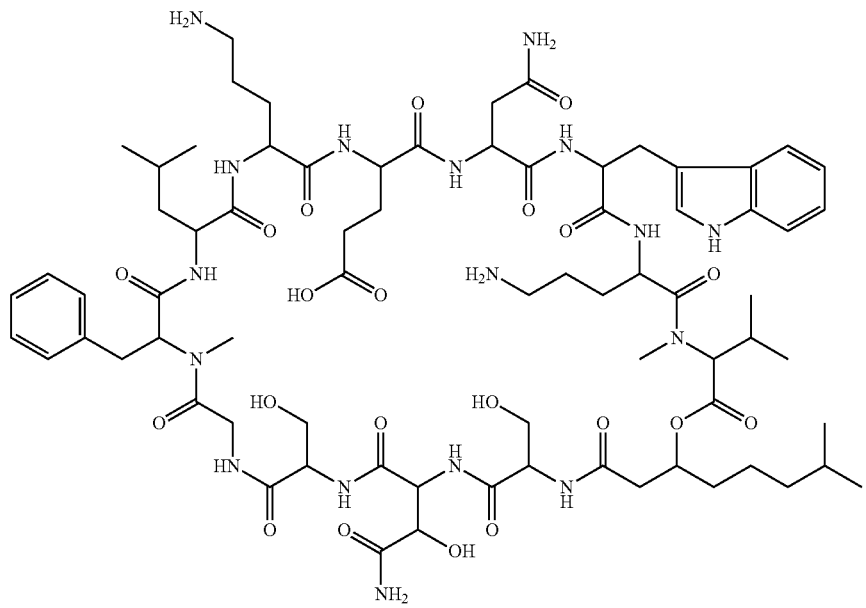

The depsipeptide antibiotic drug including lotilibcin may be used in the form of its pharmaceutically acceptable salt. Examples of such a pharmaceutically acceptable salt are inorganic acid salts such as a hydrochloride, hydrobromide, hydroiodide, and the like as well as organic acid salts such as a tartarate, citrate, toluenesulfonate, and the like. A particularly preferred salt of lotilibcin is its dichloride.

The amount of the depsipeptide antibiotic drug in the external formulation according to the present invention is set such that it can exert its antibacterial activity significantly when combined with boric acid, although the particular amount may be selected depending on various factors including the type of the target bacteria in interest, the type or seriousness of the infectious disease to be treated, the affected site in the body, the intention of the formulation which is used for prevention or treatment, the dosage form of the formulation. The minimal amount of the depsipeptide antibiotic drug in the formulation is preferably at least 0.01%, more preferably 0.05%, and most preferably 0.1% by weight, while the maximal amount thereof is preferably about 5.0%, more preferably 2.5%, further-more preferably 2.0%, and most preferably 1.0% by weight. More specifically, the amount of lotilibcin or other depsipeptide antibiotic drug in the final formulation is preferably from 0.01% to 5.0% by weight, more preferably from 0.05% to 2.5%, further more preferably from 0.05% to 2.0%, and most preferably from 0.1% to 1.0% by weight of the final formulation. In a preferred topical formulation, the composition is presented in 50 or 100 gram tubes and the composition is administered to an affected area of a patient or subject by rubbing an effective amount (often about 1-2 grams) of the composition four or five times a day onto the area. Typically, such composition will administer about 100-500 mg or more of boric acid, preferably up to about 250 mg of boric acid and about 2.5 to 15 mg, preferably up to about 10 mg depsipeptide (preferably lotilibicin) per day to the affected area of the patient or subject.

Boric acid which is added for the purpose of enhancing the antibacterial activity of a depsipeptide antibiotic drug such as lotilibcin according to the present invention may be used in the form of its salt such as sodium borate (borax) and ammonium borate or its ester which is acceptable as an additive in a pharmaceutical preparation. In such case, the amount (weight) of sodium borate, ammonium borate or its corresponding ester ("boric acid chemical agent") in the final formulation is adjusted to conform to the amount of boric acid typically used in the present invention. Thus, the weight of the boric acid chemical agent is included in the final formulations in an amount equal to the molar equivalent of boric acid used (as described above). By way of example, the amount of boric acid used in the present formulations is converted to a molar equivalent of the boric acid chemical agent used in order to determine the amount (weight) of the boric acid chemical agent to be included in the present formulations. The amount of boric acid chemical agent which is converted from the amount of boric acid falls within the aforementioned range set forth above.

The amount of boric acid which is added is at least 0.01% by weight of the final formulation since it has been ascertained that the antibacterial activity of lotilibcin can be enhanced in the presence of such an amount of boric acid. The minimal amount of boric acid is preferably 0.05% and more preferably 0.1%, while the maximal amount thereof is preferably 5.0%, more preferably 2.5%, further more preferably 2.0%, and most preferably 1.0% by weight. More specifically, the amount of boric acid is preferably from 0.01% to 5.0%, more preferably from 0.05% to 2.5%, further more preferably from 0.05% to 2.0%, and most preferably from 0.1% to 1.0% by weight. The amount of boric acid chemical agent used is generally more than the above range for boric acid, given that the boric acid chemical agents which may be substituted for boric acid generally have molar weights which are larger than that for boric acid.

Boric acid (also called boracic acid) has a very long history as a compound which is used in the medical field. In 1702, Wilhelm Homberg, a Dutch chemist produced it as a crystalline compound by distillation of a mixture of iron sulfate and borax. Later in 1876, Joseph Lister, a British surgeon proposed to use boracic lint (made from surgical lint which was soaked in a boiled boric acid solution and then dried) for a disinfection purpose.

In Japan, boric acid was listed in the past in the Pharmacopeia of Japan as a drug in the form of boric acid ointment and boric acid and zinc oxide ointment both containing a large amount of boric acid on the order of 10% (w/v). However, in view of poisoning cases by boric acid occurred in Japan and abroad and safety concerns by percutaneous absorption, 10% boric acid ointment and 10% boric acid and zinc oxide ointment were considered to be "not useful" and "not meaningful as an additive", respectively, in the Drug Efficacy Reevaluation—Drugs for Medical Use, Part 24, 1985 (published on Jul. 30, 1985 in Yakuhatsu No. 755 by the Ministry of Health and Welfare in Japan). As a result, boric acid ointment, boric acid and zinc oxide ointment, and even glycerin borax were deleted from the Pharmacopeia and the standard prices for medicine in Japan.

Consequently, nowadays only a low concentration of boric acid (an aqueous solution containing 2% or less boric acid) is allowed to use in ophthalmology for the purpose of "washing and disinfecting against conjunctival sacs". Besides, such a low (at most 2%) concentration of boric acid at which no positive therapeutic efficacy is exerted can be used as a pharmaceutical additive for use as a stabilizer, buffer agent, tonicity agent, pH adjusting agent, antiseptic, preservative, solubilizing agent or the like. For this purpose, boric acid is allowed to be used in a concentration of up to 18 mg/g (1.8% (w/w)) for external (percutaneous) application, up to 20 mg/mL (2.0% (w/v)) for ophthalmic use, and up to 20 mg/mL (2.0% (w/v)) for otolaryngology use in Japan.

Thus, despite the history that boric acid had been regarded as useful to a certain degree for medical application when used in a high concentration on the order of 10%, after it was known that such a high concentration of boric acid causes safety problems overcoming its effectiveness, the usefulness of boric acid in the medical field was denied by a medical authority, and it has become a compound which cannot be put into practical use as a sole active ingredient. On the other hand, at a low concentration of 2% or less, boric acid does not exhibit any effectiveness qualified as a drug active ingredient, so it is merely used in ophthalmology for the purpose of washing or in external drug applications as an additive for the purposes of drug stabilization, buffering, tonicity adjustment, solubilization, pH adjustment, and sterilization/preservation, for which alternative choices exist.

Definitions of Bacteria

The external formulation according to the present invention is intended to treat infection by Gram-positive bacteria such as *Staphylococcus aureus, Staphylococcus epidermidis, Propionibacterium, Bacillus*, which include drug-resistant bacteria (e.g. Methicillin Resistant *Staphylococcus aureus* aka MRSA) and on which a depsipeptide antibiotic drug exemplified by lotilibcin exhibits an antibacterial activity.

*Staphylococcus aureus* is a species of bacteria normally existing on the skin, naris or other site of a human being or mammal and causes topical infections arising from a cut, stab or other wound in the skin and various infections on the eye, ear or nose. With progression of the symptoms caused by the infection with such bacteria, they may result in life-threatening serious infectious diseases such as pneumonia, peritonitis, sepsis, and meningitis. This sort of bacteria, particularly those having resistance to a drug such as resistance to methicillin give rise to problems in community-acquired infections which is now expanding, in addition to nosocomial infections. Therefore, the external formulation according to the present invention is useful in prevention or treatment of topical infections or postoperative wound infections on the skin or other site and additionally in prevention of spread of bacterial infections in medical facilities or the like which is considered to be important from an aspect of public health.

*Propionibacterium acnes*, which belongs to the genus *Propionibacterium*, is involved in the occurrence of pimples (acne vulgaris and other acne conditions). The external formulation according to the present invention is also effective against this bacterium. Thus, the present formulations may be used to treat acne, wherein the acne is a condition selected from the group consisting of acne vulgaris, acne venenata, cystic acne, acne fulminans, acne papulosa, acne pustulosa, acne caused by MRSA, and nodulocystic acne and wherein the formulation further includes, in addition to an effective amount of boric acid or a boric acid chemical agent and lotilibcin, an effective amount of benzoyl peroxide, salicylic acid and/or a retinoid.

Among the genus *Bacillus*, particularly *Bacillus anthracis* is important as a causative bacterium of zoonotic infections. This sort of bacteria can spread not only by a usual contagion route but also by droplet infection. Application of the topical/external formulation according to the present invention is also useful for the purpose of obviating unanticipated infection by this bacterium.

The bacterial infections which can be prevented or treated by the topical/external formulation according to the present invention includes not only infections of human beings but also those of animals such as dogs, cats, and livestock.

Formulations and Components of the Present Invention

The topical/external formulation according to the present invention can be effectively used by topical administration to the skin, eye, ear or nose (e.g., in the form of a skin embrocation preparation, eye drops, ear drops and nasal drops), administration into the mouth in the form of a gargle, and administration into the respiratory organs in the form of an inhalant. The topical formulations may be prepared in dosage forms to be administered to the anus/rectum or vagina of a subject or patient.

Various dosage forms such as liquid (solution, suspension, emulsion, or dispersion), ointment, gel, aerosol, solid, and cream can be used.

When needed for pharmaceutical preparation, various pharmaceutically acceptable auxiliary additives such as a surfactant, excipient, oily agent, thickener, preservative, vitamin agent, pH adjusting agent, antioxidant, colorant, and flavor can be appropriately incorporated in the formulation. These additives include anionic surfactants, nonionic surfactants, amphoteric surfactants, hydrocarbons, natural oils and fats, fatty acids, higher alcohols, alkyl glyceryl ethers, esters, silicone oils, polyhydric alcohols, lower alcohols, saccharides, high molecular compounds, powder, salts, organic acids, water, and the like.

The surfactant includes nonionic surfactants such as polyoxyethylene higher fatty acid ethers, sorbitan fatty acid esters, polyoxyethylene glycol monooleate, and polyoxyethylene hydroganated castor oil, anionic surfactants such as fatty acid monocarboxylic acids, polyoxyethylene alkyl ether acetates, and polyoxyethylene alkyl sulfates, and amphoteric surfactants such as alkylamidobetaines, those of the imidazoline type, and those of the glycine type.

The excipient includes water, alcohol, glycerin, propylene glycol, polyethylene glycol, hydroxyethyl cellulose, sorbitol, carboxymethyl cellulose, microcrystalline cellulose, starch, dextrin, a-cyclodextrin, HP-beta Cyclodextrin, precipitated silica, and the like. The oily agent includes coconut oil, palm oil, olive oil, liquid petrolatum, squalane, petrolatum, oleic acid, cetyl alcohol, stearyl alcohol, isostearyl alcohol, dimethylpolysiloxane, polyoxyethylene stearyl ether, and the like. The thickener includes carboxyvinyl polymers, carboxymethyl cellulose, carrageenan, sodium alginate, and the like. The preservative includes benzoic acid, dehydroacetic acid, sorbic acid, benzalkonium chloride, hydroxybenzoic acid alkyl esters, and the like. The vitamin agent includes vitamin A, vitamin B, vitamin C, vitamin E, and the like. The weight ratio of depsipeptide antibiotic and boric acid mixture (X) to HP-beta Cyclodextrin (Y) X:Y is 1:16.

The topical/external formulation according to the present invention can be prepared by a general method for pharmaceutical preparations known in the art. The dosing frequency or interval is not critical, but often is administered/applied one, two, three or more times each day as is appropriate for the indication or condition to be treated. The amount of the composition applied is not generally critical to effect an intended therapeutic result provided that an effective amount is used. Often a composition comprising from 0.001 mg to 1.0 gram may be applied to a given surface of the body to effect an intended result in treating a disease state and/or condition otherwise described herein. As described above, the composition may comprise other components such as antiseptics, surface active agents, adjuvants, carriers, other active ingredients, etc. The formulation can be administered daily by a single dose or plural doses, and a longer dosing interval is possible.

The following testing examples are given for demonstrating the effect of enhancing the antibacterial activity of a depsipeptide antibiotic drug in the presence of boric acid. The depsipeptide antibiotic drug used in these examples is lotilibcin since it is representative of such a drug. The compound actually used in the examples was lotilibcin dihydrochloride.

Example 1

Assessment of the Effect of Boric Acid on the Antibacterial Activity of Lotilibcin The effect of boric acid on the antibacterial activity of lotilibcin was assessed using murine models infected by MRSA on the skin, to which single dose administration was applied to evaluate a beneficial effect. In this test, mupirocin, an external antibacterial agent which is frequently used in clinical sites was used as a comparative control (positive control).

(1-1) In Vitro Test

Prior to investigations on mice, the antibacterial activity of each compound was determined using the same bacteria as used in this efficacy evaluation test. The measurement was carried out in accordance with the standard method (broth microdilution method) specified by the Japanese Society of Chemotherapy. The medium used for culture was cation-adjusted Mueller-Hinton broth (CAMHB) to which 5% FBS (fetal bovine serum) was added or not added as a serum component.

The results are shown in Table 1. As shown therein, it was found that lotilibcin had an antibacterial activity lower than that of mupirocin in the absence of a serum component (FBS), but it exerted its antibacterial activity almost comparable to that of mupirocin in the presence of a serum component. Boric acid, when used solely, exhibited an antibacterial activity in a concentration equivalent to 0.25% (2500 μg/mL) and its activity was not influenced by the presence or absence of a serum component.

TABLE 1

| Test Substance | Presence of 5% FBS | Minimum Inhibitory Concentration Against MRSA Used in Animal Model (MIC, μg/mL) |
|---|---|---|
| Lotilibcin (sole) | No | 1 |
|  | Yes | 0.25 |
| Boric Acid (sole) | No | 2500 |
|  | Yes | 2500 |
| Mupirocin | No | 0.125 |
| (Positive Control) | Yes | 0.5 |

(1-2) Efficacy Evaluation Test on Mice

Based on the above results of in vitro measurement for antibacterial activity, an efficacy evaluation test was carried out by a single dose method using murine skin infection model with MRSA.

In this test, a low-irritative formulation was prepared for use in the test by mixing a test substance with a well-known water-soluble ointment base (glycerin) to dissolve it in the base followed by adding a pH adjusting agent sufficient to give a pH value of around 5.

This test was carried out in two steps, a preliminary test and a main test.

Preliminary Test

In the preliminary test, a single dose of various concentrations of lotilibcin or boric acid solely or 2% mupirocin (positive control) was administered to determine the dose response of each test substance with respect to antibacterial efficacy.

The preliminary test was carried out in the following manner. After an experimental heat wound site was made on the back of each mouse, $1 \times 10^6$ CFU per animal of MRSA cells was subcutaneously inoculated in the affected site to cause skin infection. The next day each test substance was percutaneously administered in a single dose to three animals per group. After one additional day had passed, a skin tissue was collected from the affected site and an increase or decrease in the number of cells (CFUs) was determined by a bacteriological technique for evaluating the effectiveness of the test substance.

TABLE 2

| Group No. | Test Substance | Route of Administration | Dose (single) |
|---|---|---|---|
| 1 | ointment base alone (negative control) | topical application (external) | 100 μL/animal |
| 2 | 2% mupirocin (positive control) | " | 100 μL/animal |
| 3 | 1% boric acid alone | " | 100 μL/animal |
| 4 | 0.1% boric acid alone | " | 100 μL/animal |
| 5 | 0.5% lotilibcin alone | " | 100 μL/animal |
| 6 | 0.2% lotilibcin alone | " | 100 μL/animal |
| 7 | 0.02% lotilibcin alone | " | 100 μL/animal |

In this test, 0.1% and 1.0% concentrations of boric acid were tested for evaluation. These concentrations were selected in view of the historical background of boric acid as discussed previously in detail. Namely, it was revealed that boric acid has a safety risk over its effectiveness in a high concentration of 10% or more. On the other hand, in a low concentration of 2% or less, boric acid does not exhibit any effectiveness qualified as a drug active ingredient, so it is merely used in ophthalmology for the purpose of washing or in external applications as an additive for the purposes of drug stabilization, buffering, tonicity adjustment, solubilization, pH adjustment, and sterilization/preservation, for which alternative choices exist The results of the preliminary test are shown in FIG. 1. As can be seen therefrom, dose-dependent efficacy was observed by sole administration of lotilibcin in concentrations of 0.02%, 0.2%, and 0.5%. The efficacy observed in a concentration of 0.5% was comparable to that of 2% mupirocin as a positive control for comparison.

Regarding boric acid on the other hand, while it had a minimum inhibitory concentration equivalent to 0.25% (2500 μg/mL) against the test microorganisms in the above-mentioned in vitro test, the change in the number of cells observed in the efficacy evaluation using animal infection models was on the same level as or worse than the result of the negative control even when administered in a concentration of 1% (10,000 μg/mL) which is 4 times as higher as its in vitro MIC value. Namely, it was found that boric acid itself had no antibacterial efficacy in concentrations ranging from 0.1% to 1% when tested with animal infection models.

Main Test

In the main test which was generally carried out in the same manner as described in the preliminary test, a formulation containing 0.5% lotilibcin and further containing 1% boric acid, which solely showed no antibacterial efficacy in the preliminary test, was prepared. A single dose of the formulation was applied to murine MRSA skin-infected models and evaluated for the efficacy in comparison with 2% mupirocin as a positive control.

TABLE 3

| Group No. | Test Substance | Route of Administration | Dose (single) |
|---|---|---|---|
| 1 | ointment base alone (negative control) | topical application (external) | 100 μL/animal |
| 2 | 2% mupirocin (positive control) | " | 100 μL/animal |
| 3 | 0.5% lotilibcin + 1% boric acid | " | 100 μL/animal |

Figure 2:
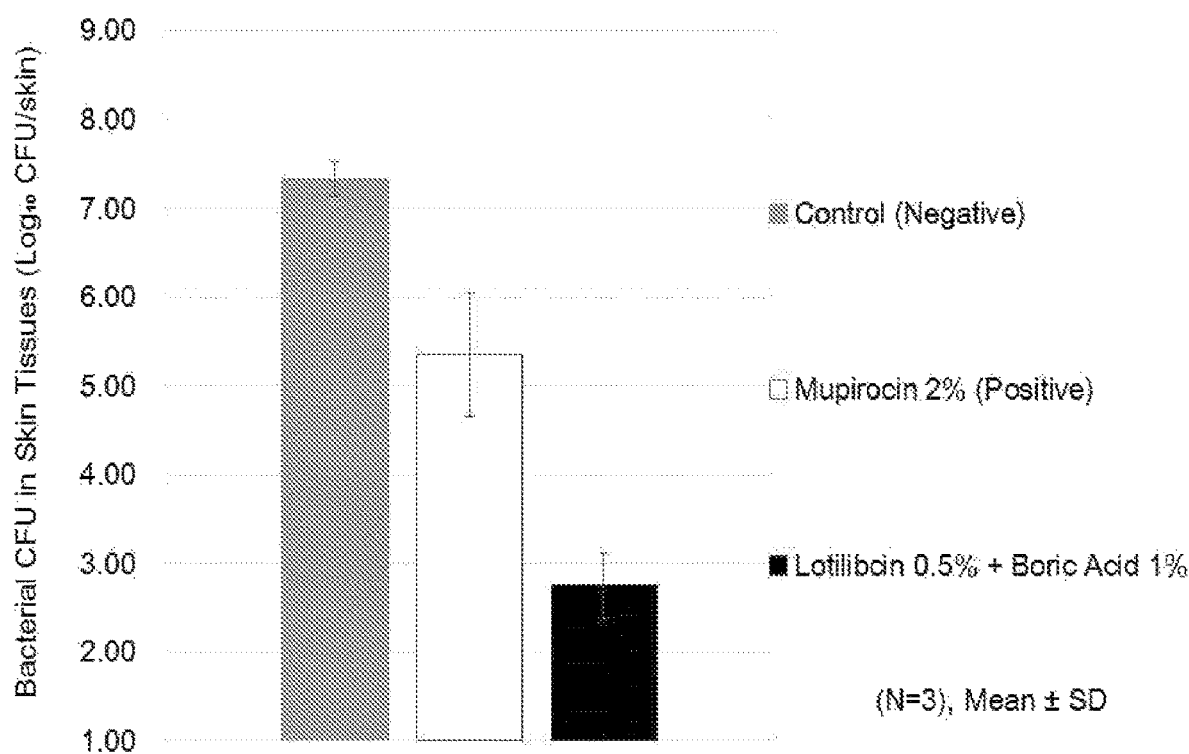
FIG. 2 A chart showing the result of an efficacy evaluation test (a main test) by single dose administration using experimental murine models infected with methicillin-resistant *Staphylococcus aureus* (MRSA) on the skin. As stated for FIG. 1, the ordinate shows the result of efficacy obtained by applying a single dose of a test substance to the skin which has been inoculated by $1\times10^6$ CFU (colony forming units) of bacterial cells, excising the infected skin tissue after 24 hours, counting the number of CFUs in the skin tissue, and evaluating the efficacy by a decrease or increase in the number of CFUs. The abscissa shows the individual test substances.

The results are shown in FIG. 2. Surprisingly it was ascertained that the group in which a formulation containing 0.5% lotilibcin along with 1% boric acid which is a low concentration having no antibacterial activity was percutaneously administered by a single dose resulted in the number of CFUs which was decreased compared to 2% mupirocin by a factor of 100, indicating a very high efficacy of the formulation.

Additional Test

Based on the new finding obtained in the main test, the present inventor carried out an additional test. In this test, a formulation having the concentrations of lotilibcin and boric acid which were decreased by half, namely to 0.25% and 0.5%, respectively, was prepared and compared to 2% mupirocin with respect to antibacterial efficacy.

TABLE 4

| Group No. | Test Substance | Route of Administration | Dose (single) |
|---|---|---|---|
| 1 | ointment base alone (negative control) | topical application (external) | 100 μL/animal |
| 2 | 2% mupirocin (positive control) | " | 100 μL/animal |
| 3 | 0.25% lotilibcin + 0.5% boric acid | " | 100 μL/animal |

Figure 3:
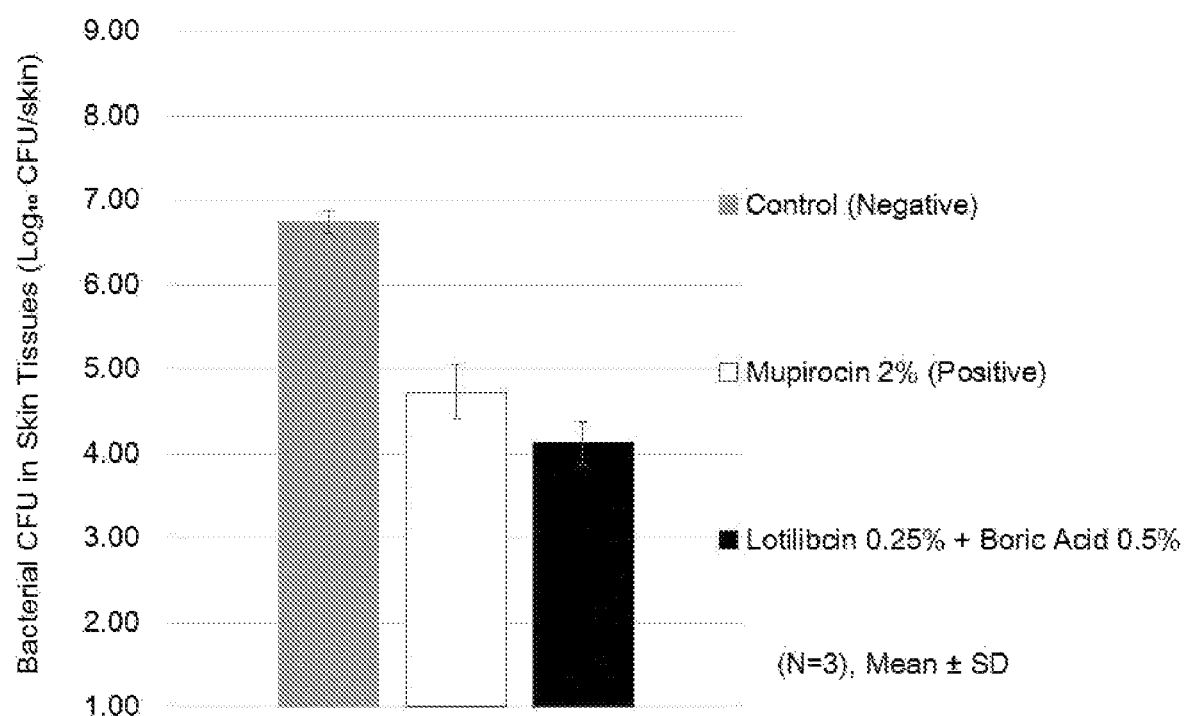
FIG. 3 A chart showing the result of an efficacy evaluation test (a preliminary test) by single dose administration using experimental murine models infected with methicillin-resistant *Staphylococcus aureus* (MRSA) on the skin. As stated for FIG. 1. the ordinate shows the result of efficacy obtained by applying a single dose of a test substance to the skin which has been inoculated by $1\times10^6$ CFU (colony forming units) of bacterial cells, excising the infected skin tissue after 24 hours, counting the number of CFUs in the skin tissue, and evaluating the efficacy by a decrease or increase in the number of CFUs. The abscissa shows the individual test substances.

As can be seen from FIG. 3 which shows the results, the formulation containing 0.25% lotilibcin and 0.5% boric acid also exhibited an antibacterial activity with a significant decrease in the number of CFUs compared to 2% mupirocin.

As evidenced from the series of investigations on efficacy evaluation described above, the present inventor succeeded in drastically increasing the efficacy profile of lotilibcin as a depsipeptide antibiotic compound by adding a low concentration of boric acid.

Use of a formulation according to the present invention makes it possible to dramatically improve the therapeutic efficacy or the protective efficacy in prevention of infections when an antibiotic drug, lotilibcin is applied as an external antibacterial agent for the purpose of treatment of various bacterial infections in human beings and animals. By this effect it is possible to greatly shorten the entire period required for treatment. As a result, an antibacterial agent for external use having high safety with a decreased dose or dosing frequency is provided in the medical field. It also contributes to suppression of appearance of drug-resistant bacteria due to a significant decrease in exposure to antibacterial drugs.

Example 2

Relation Between Antibacterial Activities in an In Vitro Test and Efficacy Evaluation in an Animal Test As a result of the efficacy evaluation in the animal test shown in Testing Example 1 above, the present inventor had the new finding that addition of boric acid had a surprisingly beneficial influence on usefulness of lotilibcin as a depsipeptide antibiotic drug for external use. This result, however, presented a new subsidiary problem which the present inventor had to face. The problem is that the efficacy data obtained from the animal evaluation tests should be reproduced in an in vitro test for antibacterial activity measurement such as an in vitro antibacterial susceptibility test which is more convenient than animal tests.

In a clinical examination department of a medical facility such as a hospital, an antibacterial agent for medical use generally receives a simple in vitro test. From the result of this test, the effectiveness of the drug when administered to a human being is predicted before actual administration of a prescribed formulation is actually started for antibacterial therapy.

In a series of in vitro investigations with no animals which the present inventor had carried out in advance, a significant increase in antibacterial activity was not observed by addition of boric acid to lotilibcin.

(2-1) In Vitro MIC Test

In order to solve the aforementioned problem, additional investigations were made so as to know the dose response of the effect of boric acid used for enhancing the antibacterial activity of lotilibcin under in vitro conditions. Namely, the antibacterial activity of lotilibcin against a clinically isolated strain of MRSA in the presence of different concentrations of boric acid was measured. The measurement was carried out in accordance with the standard method (broth microdilution method) specified by the Japanese Society of Chemotherapy. The medium which was used was cation-adjusted Mueller-Hinton broth (CAMHB). The concentration of lotilibcin was fixed at 1 μg/mL corresponding to the MIC of lotilibcin alone.

In this test, a serum component, FBS was used as a positive control since it was already known to enhance the antibacterial activity of lotilibcin. The antibacterial activity of boric acid alone against the bacteria used in this test was evaluated beforehand, and its anti-MRSA activity (MIC) was 2500 μg/mL (equivalent to 0.25%).

The results of this test are shown in Table 5. As can be seem from these results, in the presence of boric acid, an apparent decrease in the MIC value due to the antibacterial activity of boric acid itself was observed when the concentration of boric acid was 0.25% or higher at which boric acid had an inhibitory activity on the growth of the bacteria. However, in the aforementioned murine drug efficacy test, boric acid when used alone exhibited no antibacterial activity (efficacy). Therefore, it became clear that the results obtained in this in vitro test could not be directly correlated to the efficacy observed in the animal test (Animal testing showed synergistic enhancement of the antibacterial activity of lotilibcin by addition of boric acid).

In this in vitro test, a concentration of boric acid of 0.1% or less did not exhibit any enhancement of the antibacterial activity of lotilibcin. In the presence of 0.2% boric acid, a weak enhancement of the antibacterial activity (a small decrease in the MIC value) was observed, but of course it cannot explain the results observed in the animal test in the presence of a low concentration of boric acid.

TABLE 5

Antibacterial activity of lotilibcin against clinically isolated MRSA strain

| Additive | | Antibacterial activity (MIC, μg/mL) | Remarks |
|---|---|---|---|
| FBS | 5% | ≤0.06 | Positive control |
| Boric acid | 1% | ≤0.06 | Apparent MIC value decreased due to the antibacterial activity of boric acid itself |
| | 0.5% | ≤0.06 | |
| | 0.25% | ≤0.06 | |
| | 0.2% | 0.25 | Weak enhancement of antibacterial activity |

TABLE 5-continued

Antibacterial activity of lotilibcin against clinically isolated MRSA strain

| Additive | Antibacterial activity (MIC, μg/mL) | Remarks |
|---|---|---|
| 0.1% | 1 | No enhancement effect |
| 0.05% | 1 | of antibacterial |
| 0% | 1 | activity of lotilibcin (1 μg/mL) |

(2-2) Cross MIC Test

Since the above in vitro investigation did not bring forth a result which could successfully explain the significant enhancement of the antibacterial activity of lotilibcin in the presence of boric acid observed in the animal test, the present inventor made an additional investigation for more fully evaluating the effect of boric acid when added to lotilibcin. Namely, the antibacterial activity against MRSA was determined with varying concentrations of the two test substances (lotilibcin and boric acid) in a cross manner (cross MIC test). The measurement was carried out in accordance with the standard method (broth microdilution method) specified by the Japanese Society of Chemotherapy. The medium used for culture was cation-adjusted Mueller-Hinton broth (CAMHB). The medium was inoculated with $2 \times 10^5$ CFU/well of MRSA and incubated for 20 hours at 37° C. The presence or absence of bacterial growth was determined under the conditions with varying concentrations of the two test substances. The test results are shown in Table 6.

TABLE 6

Incubated in cation-adjusted Mueller-Hinton broth for 20 hours at 37° C.

| Boric acid (μg/mL) | 0 | 313 | 625 | 1250 | 2500 | 5000 |
|---|---|---|---|---|---|---|
| Lotilibcin 8.0 | – | – | – | – | – | – |
| (μg/mL) 4.0 | – | – | – | – | – | – |
| 2.0 | – | – | – | – | – | – |
| 1.0 | – | – | – | – | – | – |
| 0.5 | + | + | + | – | – | – |
| 0.25 | + | + | + | + | – | – |
| 0.125 | + | + | + | + | – | – |
| 0 | + | + | + | + | – | – |

(+): presence of growth;
(–) absence of growth (+): presence of growth; (–) absence of growth Calculation of FIC Index as Indicator of Synergy From these results, the cross MIC value of each test substance (the minimum inhibitory concentration in the presence of the other component) was read, and the counteraction between these substances was evaluated by the FIC (Fractional Inhibitory Concentration) index calculated by the following equation:

$$FIC\ index^* = \frac{MIC\ \text{value of substance } A \text{ when combined with substance } B}{MIC\ \text{value of substance } A \text{ when used alone}} + \frac{MIC\ \text{value of substance } B \text{ when combined with substance } A}{MIC\ \text{value of substance } B \text{ when used alone}}$$

* ≤0.5: synergistic effect, >0.5 and ≤1.0: additive effect;

\>1.0 and ≤2.0: no effect, >2.0: counter effect

Regarding the effect of combined use of lotilibcin and boric acid, the FIC index of these two substances calculated by the above equation is 1.0, indicating that no or only a very weak effect was obtained by the combined use.

(2-3) Additional Cross MIC Test Using 5% FBS

In order to elucidate the cause why the in vitro antibacterial activity of lotilibcin evaluated in the presence of boric acid did not correlate to the above-discussed data obtained in the animal efficacy evaluating test, the effect of boric acid on the antibacterial activity of lotilibcin was again tested under conditions which were made closer to a living body by addition of FBS as a serum component to a basal medium. More specifically, 5% FBS was added to cation-adjusted Mueller-Hinton broth (CAMHB) before this test medium was used and the cross MIC test was carried out in the same manner as mentioned in (2-2) above.

As a result, surprisingly the FIC index for evaluating the effect of combined use of lotilibcin and boric acid decreased to 0.25, a value indicating synergistic interaction. Thus, the present inventor succeeded in ascertaining the very high synergistic effect of boric acid on the antibacterial activity of lotilibcin in an in vitro test. These results also correlated to the finding obtained in the above-discussed animal test for efficacy evaluation. The test results are shown in Table 7. In table 7, the point of synergy at Boric Acid is 313 μg/mL or 5.0 mM/mL for Boric Acid, and for Lotilibcin, 0.03 μg/mL is 18 nM/mL.

TABLE 7

Incubated in 5% FBS-added cation-adjusted Mueller-Hinton broth for 20 hours at 37° C.

| Boric acid (μg/mL) | 0 | 313 | 625 | 1250 | 2500 | 5000 |
|---|---|---|---|---|---|---|
| Lotilibcin 1.0 | – | – | – | – | – | – |
| (μg/mL) 0.5 | – | – | – | – | – | – |
| 0.25 | – | – | – | – | – | – |
| 0.125 | + | – | – | – | – | – |
| 0.06 | + | – | – | – | – | – |
| 0.03 | + | – | – | – | – | – |
| 0.015 | + | + | – | – | – | – |
| 0 | + | + | + | + | – | – |

(+): presence of growth;
(–) absence of growth

The above-discussed in vitro study could reveal that an in vitro test for evaluating the antibacterial activity of lotilibcin in the presence of boric acid using a basal medium to which a certain amount (for example, a 5% solution or 0.05 g/mL) of a serum component such as FBS was added could reflectively predict the efficacy in animals and thereby demonstrate a synergistic decrease in the MIC of lotilibcin in a concentration-dependent manner.

Example 3

In this example, the effect of boric acid on the antibacterial activity of lotilibcin in the presence of a serum component was evaluated more quantitatively. Namely, the test bacteria (MRSA) and varying concentrations of one or both of the two test substances (lotilibcin and boric acid) were added to 5% FBS-added test medium (CAMHB) and incubated for 24 hours at 37° C. The number of cells in the test medium was counted after 24 hour incubation, and the intensity of antibacterial activity of lotilibcin in the presence of boric acid was evaluated. The test results are shown in Table 8.

TABLE 8

| Lotilibcin | Boric acid | Number of cells (CFU/mL) | |
|---|---|---|---|
| (μg/mL) | (μg/mL) | Initial (T = 0) | After 24 hours |
| 0.25 | — | 6.1 × $10^5$ | 2.3 × $10^5$ |
| 2.5 | — | | 7.6 × $10^2$ |
| — | 1250 | | 1.5 × $10^7$ |
| — | 2500 | | 1.9 × $10^6$ |
| 0.25 | 1250 | | 2.0 × $10^2$ |
| 2.5 | 1250 | | 0 |

In evaluation by the change (decrease) in the number of cells after 24 hour incubation as an indicator, it was ascertained that the antibacterial activity of lotilibcin tested in a medium supplemented with 5% FBS was enhanced by a factor of 1,000 by the presence of boric acid compared to that obtained with lotilibcin alone even the concentration of boric acid was as low as 1250 μg/mL which is lower than the MIC and hence does not inherently inhibit the growth of the test bacteria.

On the other hand, when boric acid was used solely for evaluation, the number of cells did not decrease after 24 hour incubation even when the concentration of boric acid was 2500 μg/mL corresponding to the MIC value. This result indicates that the boric acid itself does not have a high antibacterial activity.

Example 4

An additional in vitro test was carried out for the purpose of elucidating the minimum amount (concentration) of boric acid which could significantly enhance the antibacterial activity of lotilibcin. To a test medium which was cation-adjusted Mueller-Hinton broth (CAMHB) supplemented with 5% FBS a serial dilution of lotilibcin in the range of 0.015-8 μg/mL and a low concentration of boric acid which was 10 μg/mL (0.001%), 100 μg/mL (0.01%), or 300 μg/mL (0.03%) were added and used as a sample for evaluation. The antibacterial activity of each sample against MRSA was measured. The measurement was carried out in accordance with the standard method (broth microdilution method) specified by the Japanese Society of Chemotherapy.

As a result, it was found that the minimum concentration of boric acid necessary for enhancing the anti-MRSA activity of lotilibcin was 100 μg/mL (0.01%), which was as small as one twenty-fifth the 2500 μg/mL concentration which corresponds to the MIC when boric acid was tested solely. The test results are shown in Table 9.

TABLE 9

Antibacterial activity of lotilibcin in the presence of different concentrations of boric acid

| Boric acid (μg/mL) | Antibacterial activity of lotilibcin (MIC, μg/mL) |
|---|---|
| 300 | 0.03 |
| 100 | 0.125 |
| 10 | 0.25 |
| 0 | 0.25 |

Example 5

As an approach for assessing the usefulness of a formulation comprising lotilibcin and boric acid, the influence of the formulation on appearance of resistance was studied based on the in vitro test results in Testing Examples 2-4 by evaluating the acquisition of resistance to MRSA by an incremental subculture method in the following manner. Initially, the MIC value of a test substance in a test medium which was cation-adjusted Mueller-Hinton broth (CAMHB) supplemented with 5% FBS against growth of test bacteria (first generation bacteria) was determined in the conventional manner. Then a tested broth having a concentration of the test substance which corresponded to ¼ the MIC value was sampled and cultured on a suitable growth medium such as agar. The bacteria grown on the growth medium was isolated as second generation bacteria and used to inoculate a test broth which was subjected to MIC measurement. The bacterial growth and isolation process and the MIC measurement were repeated in the same way until the MIC value of third generation bacteria was determined. The measurement of an antibacterial activity (MIC value) was carried out in accordance with the standard method (broth microdilution method) specified by the Japanese Society of Chemotherapy. The results were evaluated by comparing the MIC value obtained with the first generation bacteria to that with the third generation bacteria. In the case where an in increase in the MIC value was found, it was concluded that resistance acquisition had occurred, and the result was evaluated by the degree of increase (numeral comparison). In this case, a minor amount of a tested broth of the third generation having a concentration which corresponded to ¼ the MIC value was sampled and cultured on agar to observe the morphological features of the colonies.

As a result, with the bacteria of the third generation, the MIC value of lotilibcin when tested solely increased to 32 μg/mL while the increase remained at 8 μg/mL when tested in the presence of boric acid. Thus, it was elucidated that administration of lotilibcin along with boric acid had the effect of retarding the induction of drug-resistant bacteria. With respect to the colony morphology of the third generation bacteria, whether lotilibcin was used alone or in combination with boric acid, the growth of colonies was slower compared to the first generation bacteria and resulted in colonies having a smaller diameter. They were found to be small colony variants (SCV's). The test results are shown in Table 10.

TABLE 10

| | Test substance | MIC in the presence of 5% FBS (μg/mL) |
|---|---|---|
| Anti-MRSA activity of 1st generation | Lotilibcin alone | 0.25 |
| | Boric acid alone | 2500 |
| Anti-MRSA activity of 3rd generation | Lotilibcin alone | 32 |
| | Boric acid alone | 5000 |
| | Lotilibcin + boric acid (625 μg/mL) | 8 |

Example 6

In view of the usefulness of boric acid in enhancing the anti-MRSA activity of lotilibcin demonstrated in the preceding examples, an in vitro screening test was carried out in order to check if the same usefulness is exhibited with bacteria other than MRSA. Various types of Gram-positive cocci were tested in an appropriately selected test medium in the absence or presence of 5% FBS to determine the antibacterial activity of lotilibcin, thereby searching for bacterial species against which lotilibcin had its antibacterial activity which was enhanced by addition of serum. In this screening test, boric acid was not used. The measurement was carried out in accordance with the standard method (broth microdilution method) specified by the Japanese Society of Chemotherapy.

As a result, it was found that the antibacterial activity of lotilibcin was enhanced by addition of 5% FBS to a culture medium when tested with *Bacillus subtilis, Bacillus anthracis* both belonging to the genus *Bacillus*, a kind of Gram-positive bacilli, and *Propionibacterium* bacteria including *Propionibacterium acnes* which causes acne vulgaris. Thus, these bacterial species meet the conditions that the antibacterial activity of lotilibcin may further be enhanced by use of boric acid in combination with lotilibcin. The test results are shown in Table 11.

TABLE 11

| Test bacteria (Gram-positive) | Antibacterial activity of lotilibcin in the absence or presence of serum (5% FBS) (MIC, μg/mL) | |
|---|---|---|
| | No serum | With serum |
| Bacillus subtilis | 2.0 | 0.25 |
| Bacillus anthracis | 1.0 | 0.1 |
| Propionibacterium acnes | 1.0 | <0.125 |

Example 7

Since the three bacterial species shown in Table 11 meet the conditions that lotilibcin has an antibacterial activity thereon and its activity is enhanced by addition of a serum component, it was expected that the antibacterial activity of lotilibcin may be further enhanced by use of boric acid in combination with lotilibcin.

In order to validate this thought, *Propionibacterium acnes* which causes acne vulgaris and pyoderma and which is clinically important as drug-resistant bacteria was tested for quantitative evaluation of the effect of boric acid on the antibacterial activity of lotilibcin in the presence of a serum component in the same manner as already conducted with MRSA. Namely, *Propionibacterium acnes* as test bacteria and different concentrations of test substances were added to a test medium supplemented with 5% FBS, and after incubation at 37° C. for a certain period of time, the number of cells in the medium was counted to evaluate the antibacterial activity of lotilibcin in the presence of boric acid. Since *Propionibacterium acnes* is anaerobic unlike MRSA, a GAM (Gifu anaerobic medium) agar was used as a test medium and incubation was carried out anaerobically (using an oxygen scavenger and a carbon dioxide gas generating agent) for 48 hours. The concentration of boric acid used along with lotilibcin was 625 μg/mL (equivalent to 0.0625%) since the antibacterial activity (MIC) of boric acid alone against the test bacteria was determined to be 1250 μg/mL (equivalent to 0.125%) in a test conducted beforehand.

As a result, when the change (decrease) in the number of cells after 48 hour incubation was used as an indicator for evaluation, it was ascertained that the antibacterial activity of lotilibcin tested in a 5% FBS-supplemented medium was enhanced by a factor of 10,000 by the presence of boric acid compared to that obtained with lotilibcin alone even the concentration of boric acid was as low as 625 μg/mL which is lower than the MIC and hence does not inherently inhibit the growth of the test bacteria. The test results are shown in Table 12.

TABLE 12

| Test substance | Number of cells (CFU/mL) | |
|---|---|---|
| | Initial (T = 0) | After 48 hours |
| Lotilibcin (0.1 μg/mL) alone | $2.8 \times 10^6$ | $1.3 \times 10^6$ |
| Lotilibcin (0.1 μg/mL) + boric acid (625 μg/mL) | | $5.3 \times 10^2$ |

As discussed above, the present inventor succeeded in drastically enhancing the efficacy profile of lotilibcin, a depsipeptide antibiotic drug, for external use by addition of a low concentration of boric acid which does not afford a pharmacological (antibacterial) activity by itself.

In addition, the testing conditions for an in vitro test for evaluating the antibacterial activity of lotilibcin in such a manner that correlates to efficacy data obtained with animal infection models could be revealed. Such testing conditions are important when a drug is put into practical use in human beings.

Lotilibcin exerts its antibacterial activity against MRSA in a concentration of 1.0 μg/mL or hither when tested by a conventional in vitro antibacterial evaluation test. In contrast, when tested by the above-mentioned testing method in which a test medium supplemented with FBS is used and boric acid is added, it is possible to demonstrate the antibacterial activity of lotilibcin in a concentration in the range of 0.015-0 1.0 μg/mL or lower. The results obtained in this in vitro test can be applied to prediction of efficacy in animals or human beings.

The dose of boric acid which is added is desirably at most a half the minimum inhibitory concentration of boric acid when tested alone against the bacteria in interest. Therefore, a desirable dose of boric acid is in the range of 100-1250 μg/mL (0.01%-0.125%) and preferably in the range of 100-625 μg/mL (0.01%-0.0625%). As mentioned previously, boric acid can be replaced by a borate compound such as sodium borate with a molar equivalent dose.
(Note: These ranges of boric acid concentration are not reflected in the claims)

FORMULATIONS

The present invention will be illustrated by the following examples without intention of limiting the present invention thereto.

External Formulation 1

Gel ointment formulations 1A and 1B having the compositions shown in Table 13 below were prepared by mixing together the individual ingredients by stirring so as to form a homogeneous solution. The pH adjusting solution which was used was a phosphate buffer prepared by mixing 39 volumes of 100 mM disodium hydrogen phosphate and 61 volumes of 100 mM sodium dihydrogen phosphate followed by adding a 0.1N sodium hydroxide solution in an amount sufficient to be diluted to 0.02N.

TABLE 13

|   | Ingredient | Amount (wt %) | |
|---|---|---|---|
|   |   | Formulation 1A | Formulation 1B |
| 1 | Lotilibcin | 0.5 | 0.25 |
| 2 | Boric acid | 1.0 | 0.5 |
| 3 | Propylene glycol | 15.0 | 15.0 |
| 4 | Methyl p-hydroxybenzoate | 0.2 | 0.2 |
| 5 | Propyl p-hydroxybenzoate | 0.03 | 0.03 |
| 6 | Hydroxyethyl cellulose | 1.5 | 1.5 |
| 7 | Sorbitol | 5.0 | 5.0 |
| 8 | Ethylenediamine tetra-acetic acid | 0.17 | 0.17 |
| 9 | pH adjusting solution | 20.0 | 20.0 |
| 10 | Purified water | 56.6 | 57.35 |
|   | Total | 100 | 100 |
|   | pH | 5.0 | 5.2 |
|   | Appearance | Translucent gel | Translucent gel |

When these formulations 1A and 1B were left for one month at 25° C. in order to evaluate the stability of appearance, no change in color and other physical properties which is problematic in pharmaceutical preparations was observed in either formulation. When subjected to a skin irritation test using a guinea pig, they showed a sufficiently low irritation.

External Formulation 2

Cream formulations 2A and 2B having the compositions shown in Table 14 below were prepared by mixing together the individual ingredients by stirring so as to form a homogeneous solution.

TABLE 14

|   | Ingredient | Amount (wt %) | |
|---|---|---|---|
|   |   | Formulation 2A | Formulation 2B |
| 1 | Lotilibcin | 0.5 | 0.25 |
| 2 | Boric acid | 0.5 | 0.5 |
| 3 | Propylene glycol | 15.0 | 15.0 |
| 4 | Methyl p-hydroxybenzoate | 0.2 | 0.2 |
| 5 | Propyl p-hydroxybenzoate | 0.03 | 0.03 |
| 6 | White petrolatum | 5.0 | 5.0 |
| 7 | Cetyl alcohol | 3.0 | 3.0 |
| 8 | Stearyl alcohol | 2.0 | 2.0 |
| 9 | Hydroxyethyl cellulose | 0.3 | 0.3 |
| 10 | Polyoxyethyelene stearyl ether | 5.0 | 5.0 |
| 11 | pH adjusting solution* | 20.0 | 20.0 |
| 12 | Purified water | 48.47 | 48.72 |
|   | Total | 100 | 100 |
|   | pH | 4.7 | 4.9 |
|   | Appearance | Slightly ash-yellowish cream with a low viscosity | |

*The same pH adjusting solution as used in Formulation 1.

When these formulations 2A and 2B were left for one month at 25° C. in order to evaluate the stability of appearance, no change in color and other physical properties which is problematic in pharmaceutical preparations was observed in either formulation. When subjected to a skin irritation test using a guinea pig, they showed a sufficiently low irritation.

External Formulation 3

Eye drop formulations 3A and 3B which also can be applied to the ear and nose and which had the compositions shown in Table 15 below were prepared by mixing together the individual ingredients by stirring so as to form a homogeneous solution.

TABLE 15

|   | Ingredient | Amount (wt %) | |
|---|---|---|---|
|   |   | Formulation 3A | Formulation 3B |
| 1 | Lotilibcin | 0.25 | 0.1 |
| 2 | Boric acid | 0.5 | 0.5 |
| 3 | α-Cyclodextrin | 2.5 | 1.0 |
| 4 | Glycerol | 2.5 | 2.5 |
| 5 | Benzyl alcohol | 0.1 | 0.1 |
| 6 | pH adjusting solution* | 20.0 | 20.0 |
| 7 | Purified water | 74.15 | 75.8 |
|   | Total | 100 | 100 |
|   | pH | 6.7 | 7.1 |
|   | Appearance | Colorless clear fluid | |

*The same pH adjusting solution as used in Formulation 1.

When these formulations 3A and 3B were left for one month at 25° C. in order to evaluate the stability of appearance, no change in color and other physical properties which is problematic in pharmaceutical preparations was observed in either formulation. When subjected to an ophthalmic mucous membrane irritation test using a rabbit, they showed a good tolerability with no abnormalities.

External Formulation 4

Aqueous inhalant formulations 4A and 4B which having the compositions shown in Table 16 below were prepared by mixing together the individual ingredients by stirring so as to form a homogeneous solution.

TABLE 16

|   | Ingredient | Amount (wt %) | |
|---|---|---|---|
|   |   | Formulation 4A | Formulation 4B |
| 1 | Lotilibcin | 0.5 | 0.1 |
| 2 | Boric acid | 0.05 | 0.05 |
| 3 | α-Cyclodextrin | 2.5 | 1.0 |
| 4 | Carboxymethyl cellulose sodium | 0.2 | 0.2 |
| 5 | Glycerol | 2.0 | 2.0 |
| 6 | pH adjusting solution* | 20.0 | 20.0 |
| 7 | Purified water | 74.75 | 76.65 |
|   | Total | 100 | 100 |
|   | pH | 6.9 | 7.2 |
|   | Appearance | Colorless clear fluid | |

*The same pH adjusting solution as used in Formulation 1.

When these formulations 4A and 4B were left for one month at 25° C. in order to evaluate the stability of appearance, no change in color and other physical properties which is problematic in pharmaceutical preparations was observed in either formulation. When subjected to an oral mucous membrane irritation test using a guinea pig, they showed a good tolerability with no abnormalities.

External Formulation 5

Lotion formulations 5A and 5B having the compositions shown in Table 17 below were prepared by mixing together the individual ingredients by stirring so as to form a homogeneous solution.

TABLE 17

| | Ingredient | Amount (wt %) Formulation 5A | Formulation 5B |
|---|---|---|---|
| 1 | Lotilibcin | 0.5 | 0.25 |
| 2 | Boric acid | 1.0 | 0.5 |
| 3 | Sorbitol | 2.5 | 2.5 |
| 4 | Glycerol | 1.0 | 1.0 |
| 5 | Carboxymethyl Cellulose sodium | 2.0 | 3.0 |
| 6 | Microcrystalline Cellulose | 2.0 | 3.0 |
| 7 | pH Adjusting Solution* | 20.0 | 20.0 |
| 8 | Purified water | 71.0 | 69.75 |
| | Total | 100 | 100 |
| | pH | 5.0 | 5.3 |
| | Appearance | Lotion-like fluid with a slightly grayish white color | |

*The same pH adjusting solution as used in Formulation 1.

When these formulations 5A and 5B were left for one month at 25° C. in order to evaluate the stability of appearance, no change in color and other physical properties which is problematic in pharmaceutical preparations was observed in either formulation. When subjected to a skin irritation test using a guinea pig, they showed a sufficiently low irritation.

External Formulation 5

Topical formulations 6A and 6B having the compositions are shown in Table 18 below. These are prepared by mixing the components together and forming a homogenous composition. 100 grams of the topical formulation may be readily made using the following components.

TABLE 18

| | Ingredient | Amount (wt %) Formulation 6A | Formulation 6B |
|---|---|---|---|
| 1 | Lotilibcin | 0.5-3.0 g | 2.0 g |
| 2 | Boric acid | 1.0-7.5 | 5.0 g |
| 3 | Sorbitol | 1.5-4.0 | 2.5 |
| 4 | Glycerol | 0.5-1.5 | 1.0 |
| 5 | Carboxymethyl cellulose sodium | 2.0-4.0 | 3.0 |
| 6 | Microcrystalline cellulose | 1.5-4.0 | 3.0 |
| 7 | pH adjusting solution* | 20.0 | 20.0 |
| 8 | Purified water | Add to 100 g Total | 63.5 |
| | Total | 100 | 100.0 |
| | pH | 4.5-6.5 | 4.94 |
| | Appearance | Lotion-like fluid with off-white color | |

*The same pH adjusting solution as used in Formulation 1.

This formulation may be applied to an infection on the surface or wound of a patient or subject. In practice, approximately 0.5-1.5 grams of the lotion are administered 2-4 times daily to the infected area. The formulations provide synergistic antibacterial activity against bacterial infections, including MRSA.

INDUSTRIAL APPLICABILITY

The present invention provides a new external formulation of a depsipeptide antibiotic drug having a high therapeutic or prophylactic efficacy for topical infections caused by the target bacteria and capable of suppressing development of drug-resistant bacteria when a depsipeptide antibiotic drug, particularly lotilibcin is topically administered as an external antibacterial drug for treatment of various bacterial infections of human beings and animals.

The abovementioned effect also makes it possible to greatly reduce the entire period required for treatment, resulting in providing an external antibacterial drug of high safety capable of reducing a dose or dosing frequency or suppressing development of drug-resistant bacteria by a significantly decreased exposure to antibacterial drugs. Thus, the present invention can offer an effective solution for the worldwide problem of drug-resistant bacteria.

REFERENCES

Patent Documents

U.S. Pat. No. 5,648,455 or 7,968,588
U.S. Pat. No. 7,968,588

Non-Patent Documents

*J. Am. Chem. Soc.*, Vol. 119: No. 28, 6680-6681 (1997)
*J. Antibiotics*, Vol. 51: No. 10, 929-935 (1998)

The invention claimed is:

1. An antimicrobial composition formulated for external use in prevention or treatment of a gram positive bacterial infection, comprising lotilibcin having the following chemical structure (1):

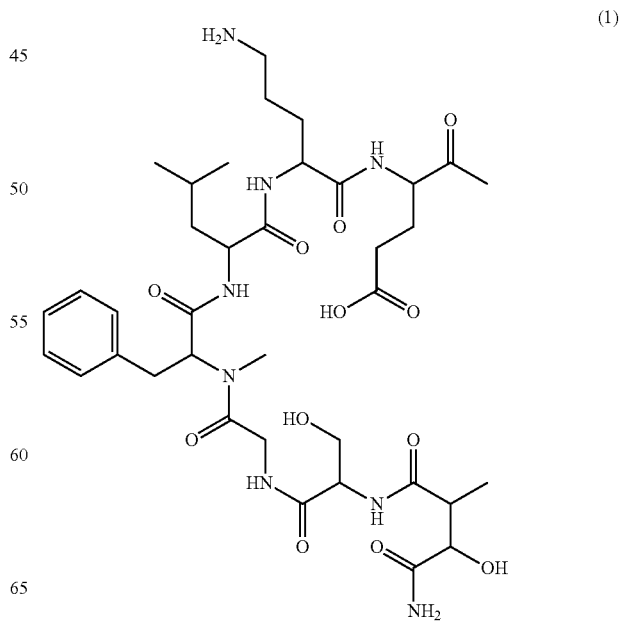

-continued

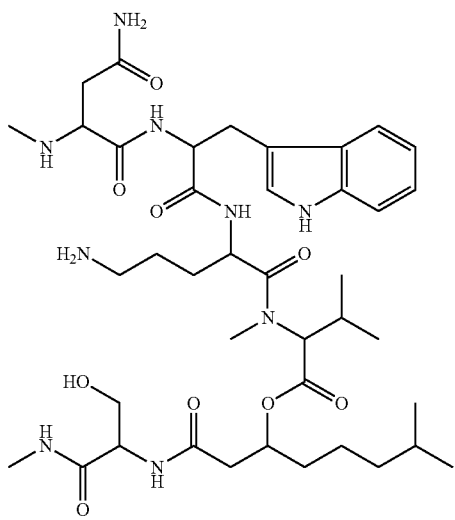

or a pharmaceutically acceptable salt or stereoisomer thereof in a concentration of at least 0.03 μg/mL in combination with boric acid in an amount of at least 0.01% by mass, wherein said combination exhibits synergistic antibacterial activity.

2. The composition of claim 1 wherein said gram positive bacteria is *Staphylococcus aureus*, or *Propionibacterium acnes*.

3. The composition of claim 2 wherein said *Staphylococcus aureus* is Methicillin Resistant *Staphylococcus aureus*.

4. The composition of claim 1, wherein said gram positive bacterial infection treated is selected from the group consisting of infections after tissue injury from burns, lacerations, abrasions, bites, surgical wounds, puncture wounds, ulcers, acute and chronic wounds from complicated skin and soft tissue infection (cSSTI), acute and chronic wounds from skin and skin structure infection (SSSI), venous stasis ulcers, diabetic ulcers, pressure ulcers, post-surgical ulcers, post traumatic ulcers and spontaneous ulcers.

5. The composition according to claim 1, wherein said lotilibcin is present in an amount of from 0.01% to 5.0% by mass.

6. The composition according to claim 5, wherein lotilibcin is present in an amount of from 0.1% to 2.5% by mass.

7. The composition according to claim 5, wherein the boric acid is present in an amount of from 0.01% to 5.0% by mass.

8. A bactericidal composition formulated for external use in the inhibition of gram positive bacterial growth in a wound or a body surface infection comprising an effective amount of boric acid and an effective amount of lotilibcin having the following chemical structure (1):

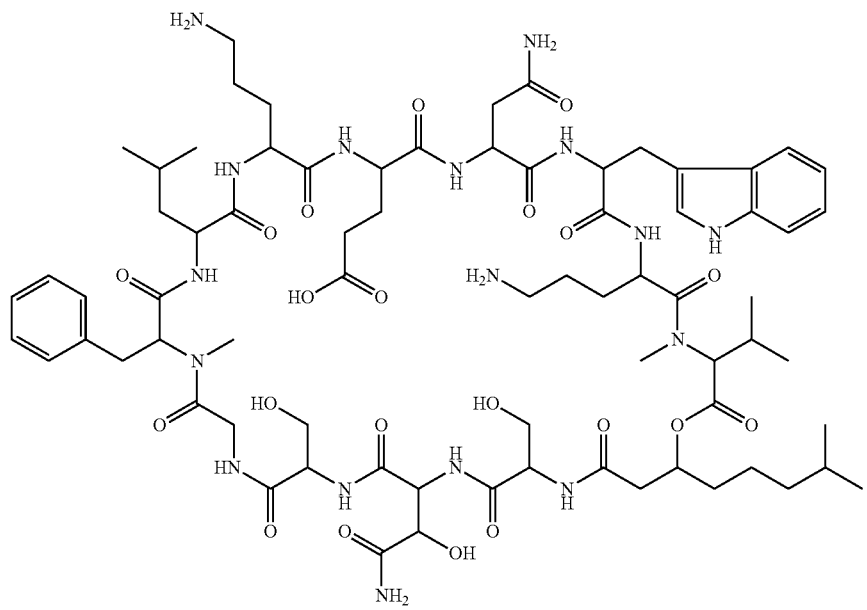 [SMILES: CC(C)CCCC1CC(=O)NC(CO)C(=O)NC(C(O)C(N)=O)C(=O)NC(CO)C(=O)NCC(=O)N(C)C(Cc2ccccc2)C(=O)NC(CC(C)C)C(=O)NC(CCCN)C(=O)NC(CCC(=O)O)C(=O)NC(CC(N)=O)C(=O)NC(Cc2c[nH]c3ccccc23)C(=O)NC(CCCN)C(=O)N(C)C(C(C)C)C(=O)O1]

or a pharmaceutically acceptable salt or stereoisomer thereof, wherein said lotilibcin exhibits sustained potency in combination with the effective amount of boric acid, wherein said combination of said lotilibcin and said boric acid exhibits synergistic antibacterial activity.

9. The composition according to claim 8 wherein said wound or body surface infection is caused by a drug resistant or multiple drug resistant gram positive bacteria.

10. The composition according to claim 9 wherein said drug resistant gram positive bacteria is Methicillin-resistant *Staphylococcus aureus*.

11. The composition according to claim 8 wherein said composition consists essentially of boric acid in a final composition ranging from at least 5.0 mM/ml (313 µg/ml) to no more than 40 mM/ml (2500 g/ml) and the concentration of lotilibcin ranges from at least 18 nM/ml (0.03 µg/ml) to 4881 nM/ml (about 8.0 µg/ml).

12. The composition according to claim 11 wherein said composition consists essentially of boric acid in a final composition ranging from at least 5.0 mM/ml (313 µg/ml) to no more than 40 mM/ml (2500 µg/ml) and the concentration of lotilibcin ranges from at least 152 nM/ml (0.25 µg/ml) to 4881 nM/ml (about 8.0 µg/ml).

13. The composition according to claim 8 formulated as an ointment, cream, lotion, salve or liquid composition for topical application and treatment of a wound, wherein said wound is medically defined as a complicated skin and soft tissue infection (cSSTI) or a complicated skin and skin structure infection (cSSSI), and said infection is an infection caused by Methicillin-resistant *Staphylococcus aureus* (MRSA).

14. The composition according to claim 8 formulated as an ointment, cream, lotion, salve or liquid composition for topical application and treatment of a wound, wherein said wound is medically defined as acne and said acne is caused by Methicillin-resistant *Staphylococcus aureus* (MRSA) or *Propionibacterium acnes*.

15. The composition according to claim 8 wherein said combination of lotilibcin and boric acid (X) also comprises HP-beta Cyclodextrin (Y) in a weight ratio X:Y of 1:16.

* * * * *